United States Patent
Goldhaber

(12) 
(10) Patent No.: US 6,234,310 B1
(45) Date of Patent: May 22, 2001

(54) STERILE PACKAGING SYSTEM

(76) Inventor: Richard P. Goldhaber, 270 Bushaway Rd., Wayzata, MN (US) 55391

( * ) Notice: Subject to any disclaimer, the term of this patent is extended or adjusted under 35 U.S.C. 154(b) by 0 days.

(21) Appl. No.: 09/389,927

(22) Filed: Sep. 3, 1999

(51) Int. Cl.[7] .................................................. A61B 19/02
(52) U.S. Cl. ........................ 206/438; 53/425; 141/92; 141/314; 383/66; 383/207; 422/28
(58) Field of Search ..................... 53/425, 426, 468, 53/469; 206/438; 422/25, 28, 40; 383/66, 207; 141/91, 92, 314, 391

(56) References Cited

U.S. PATENT DOCUMENTS

| | | |
|---|---|---|
| 4,569,377 * | 2/1986 | Ellis ....................................... 141/314 |
| 4,715,165 * | 12/1987 | Thorogood ............................. 53/469 |
| 4,907,395 | 3/1990 | Opie et al. . |
| 4,997,084 | 3/1991 | Opie et al. . |
| 5,088,617 | 2/1992 | Williams et al. . |
| 5,131,537 | 7/1992 | Gonzales . |
| 5,154,166 | 10/1992 | Chikama . |
| 5,203,458 * | 4/1993 | Cornwell ............................... 206/438 |
| 5,375,717 | 12/1994 | Roshdy . |
| 5,447,231 | 9/1995 | Kastenhofer . |
| 5,447,699 * | 9/1995 | Papciak et al. ........................ 53/425 |
| 5,497,601 | 3/1996 | Gonzalez . |
| 5,526,928 | 6/1996 | Yabe et al. . |
| 5,551,781 * | 9/1996 | Wilkes et al. ......................... 206/438 |
| 5,638,661 | 6/1997 | Banks . |
| 5,667,068 | 9/1997 | Weaver . |
| 5,699,909 | 12/1997 | Foster . |
| 6,070,397 * | 6/2000 | Bachuber ............................... 206/438 |

* cited by examiner

Primary Examiner—Stephen F. Gerrity
(74) Attorney, Agent, or Firm—Barbara A. Wrigley

(57) ABSTRACT

A packaging system for a sterilizable item comprising a pouch having a frangible opening, the pouch defining a sterile compartment therein to hold a sterilizable item and a support element for fluid attachment to a sterilizer, the support element defining a window thereupon, the support element attached to the pouch along a perimeter of the opening. The opening may comprise a scored portion cut into the front side of the pouch. The support element may be a rigid cardboard support element defining a perforated window with a knockout piece. The system may also include a cover adhered with the window for ensuring that the knockout piece remains attached to the support element until broken. The system may also include an adhesive strip attached along a perimeter of the cover, and include a removable backing strip. The present invention may also include a method of packaging a sterilizable item including providing a pouch having a frangible opening defining a sterile compartment; causing a fluid tight connection between the pouch and a sterilizer, sterilizing the exposed surfaces of the connection; breaking open the opening; passing the item through the opening into the compartment; and sealing the item inside the compartment.

16 Claims, 4 Drawing Sheets

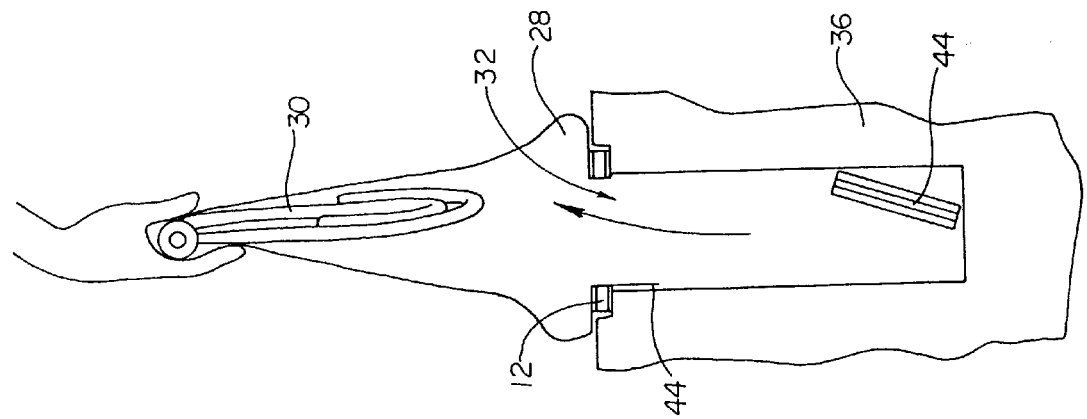
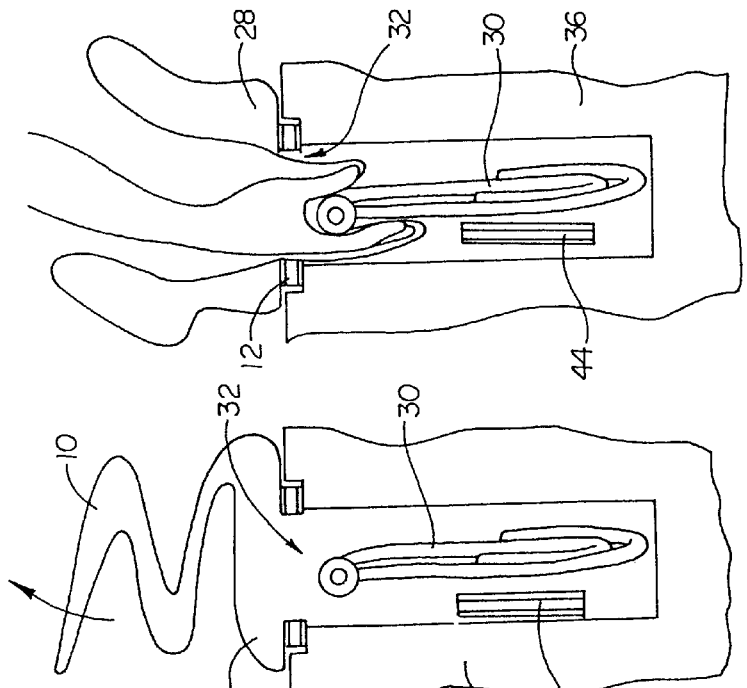
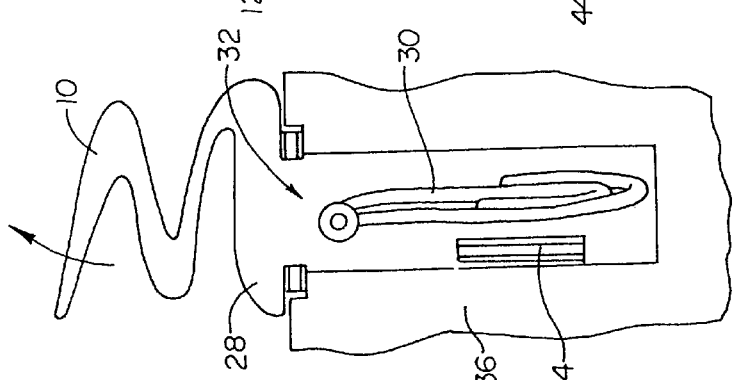
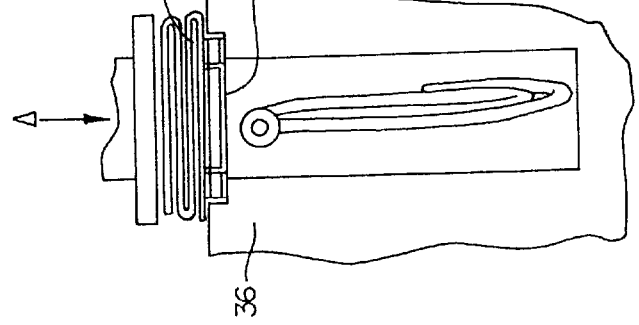

STERILE PACKAGING SYSTEM

BACKGROUND OF THE INVENTION

1. Field of the Invention

This invention is related generally to the field of sterile packaging. In particular, it relates to a device and method for sterile packaging of sterilized items such as endoscopes after reprocessing.

2. Description of the Related Art

The importance of sterile medical and dental equipment has been recognized for many years. Sterilizing dental and medical instruments prior to use may be accomplished in a number of ways such as steam or heat sterilization through autoclaving, liquid or vapor chemical sterilization through soaking, irradiation, or ethylene oxide. However, each of these methods has drawbacks. Irradiation and ethylene oxide systems require large capital expenditures. Autoclaving is limited to those items that can withstand repeated high temperatures. Liquid and vapor chemical sterilization is generally limited to surface sterilization and cannot be used to sterilize items within fluid tight packages.

Hospitals and clinics that use heat sensitive medical and dental equipment such as endoscopes are generally prefer to use liquid chemical sterilization.

However, the sterile environment of liquid chemical sterilization is breached as soon as the sterilizing system is opened. Therefore, a system is needed for long term storage that encloses the sterilizable item into a sterile portable package before the sterile environment is breached.

A new and useful sterile packaging apparatus and method is needed that overcomes the problems associated with conventional methods of sterile packaging by providing a sterile packaging system that fluidly connects to a sterilizer.

SUMMARY OF THE INVENTION

It is an object of the apparatus and method of the sterile packaging system in accordance with the present invention to solve the problems outlined above that have heretofore inhibited the successful sterilization and packaging of sterilized items after sterilization.

More particularly, the apparatus and method in accordance with the present invention provides a device for sterile packaging of sterilized items, particularly reprocessed endoscopes.

The unique sterile packaging device in accordance with the present invention broadly includes a pouch having a frangible opening, the pouch defining a sterile compartment therein to hold a sterilizable item and a support element for fluid attachment to a sterilizer, the support element defining a window thereupon, the support element attached to the pouch along a perimeter of the frangible opening.

The device in accordance with the present invention may also include a pouch that is flexible or inflatable.

The device in accordance with the present invention may also include a pouch that has a front side and a back side sealed along a perimeter thereof.

The device in accordance with the present invention may also include a frangible opening that is a rectangular portion scored into the front side of the pouch.

The device in accordance with the present invention may also include a support element that is a rectangularly shaped piece of rigid cardboard.

The device in accordance with the present invention may also include a window that is perforated with a knock out piece positioned in the window.

The device in accordance with the present invention may also include a support element that is adhesively attached along a perimeter thereof to the front side of the pouch.

The device in accordance with the present invention may also include an adhesive strip and a removable backing strip.

The device in accordance with the present invention may also include a cover adhesively in contact with the window. The window may be a perforated window with a knock out piece, wherein the cover is in contact with the window for ensuring that the knockout piece remains attached to the support element until broken open.

The device in accordance with the present invention may also include an adhesive strip and removable backing strip attached to the front side of the cover.

The device in accordance with the present invention may also include a sterilizer for use with the above packaging system.

The apparatus and method in accordance with the present invention provides a method of packaging a sterilizable item.

The method broadly includes providing a pouch defining a sterile compartment, the pouch having a frangible opening; providing a sterilizer; providing a sterilizable item; causing a fluid and microbial tight connection between the pouch and the sterilizer, the fluid tight connection having exposed surfaces; sterilizing the exposed surfaces with the sterilizer; sterilizing the sterilizable item with the sterilizer; breaking open the frangible opening; passing the sterilizable item through the frangible opening into the sterile compartment; and, sealing the sterilizable item inside the sterile compartment.

The apparatus and method in accordance with the present invention may also include manually breaking open the frangible opening and manually passing the sterilizable item through the frangible opening.

One advantage of the present invention is that the present invention provides portable sterile packaging for sterilized items.

Another advantage is that the packaging system is inexpensive.

Another advantage is that the storage system takes minimal storage space.

Another advantage is that the system of the present invention does not require a significant capital investment.

These and other objects and advantages of the present invention will become apparent during the course of the following detailed description and appended claims. The invention may best be understood with reference to the accompanying drawings, wherein an illustrative embodiment is shown.

BRIEF DESCRIPTION OF THE DRAWINGS

FIG. 4 is a partial cross sectional perspective view of a sterilizer with the device of the present invention fluidly connected to the sterilizer and a sterilizable item inside the sterilizer.

FIG. 5 is a partial cross sectional perspective view of a sterilizer with the device of the present invention with the pouch in an inflated position and with an open frangible opening and a sterilizable item in the sterilizer.

FIG. 6 is a partial cross sectional perspective view of a sterilizer with the device of the present invention with the pouch in an inflated position and with the sterilizable item being manually retrieved into the pouch.

FIG. 7 is a partial cross sectional perspective view of a sterilizer with the device of the present invention attached to the sterilizer with a sterilizable item retrieved into the sterile compartment.

DETAILED DESCRIPTION OF THE INVENTION

General Assembley

Figure 1:
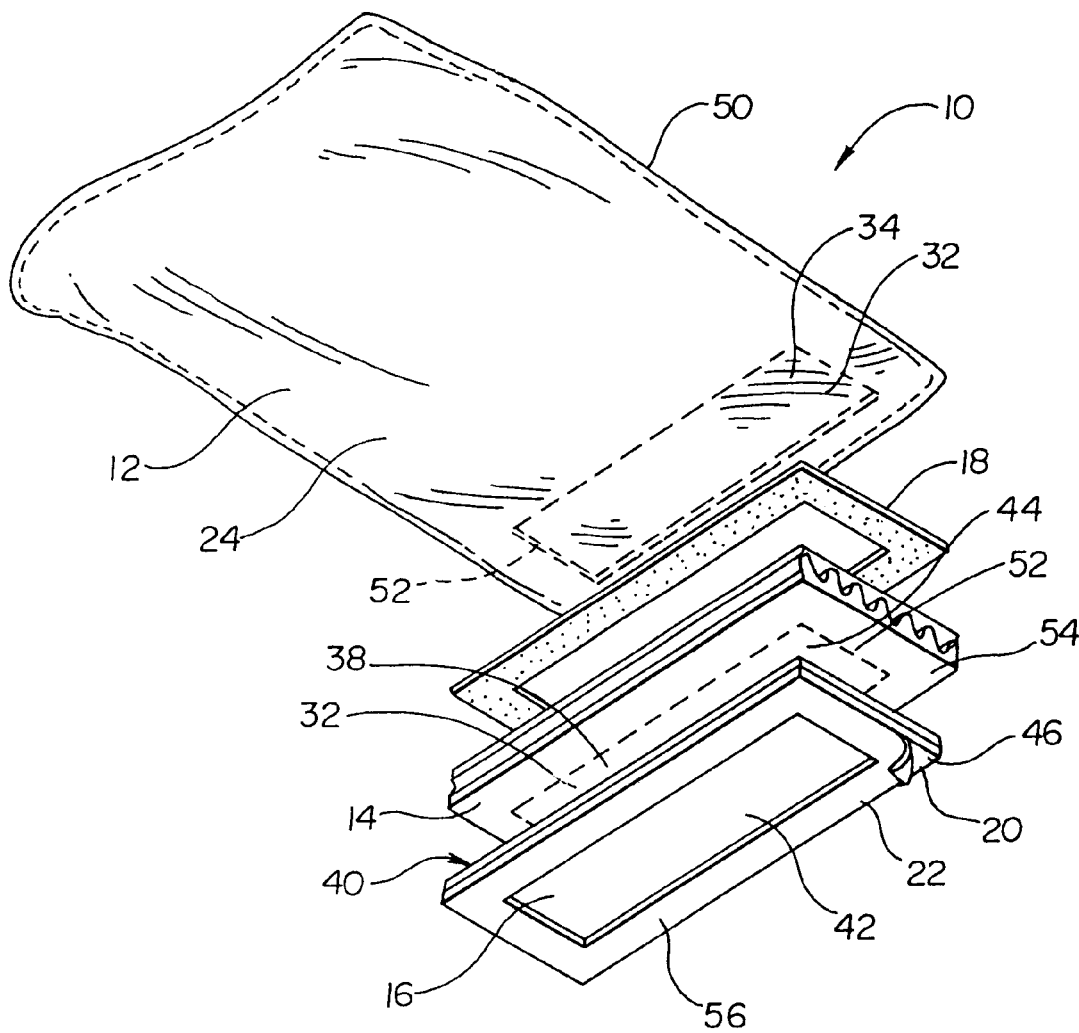
FIG. 1 is an exploded perspective view of the device of the present invention.
Figure 2:
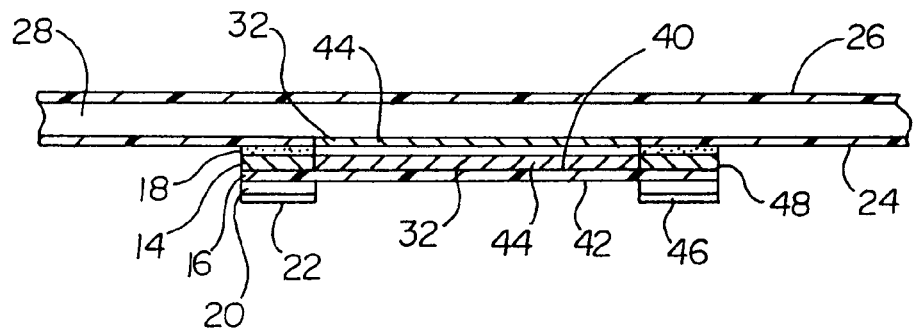
FIG. 2 is a cross sectional view of the device of the present invention.
Figure 3:
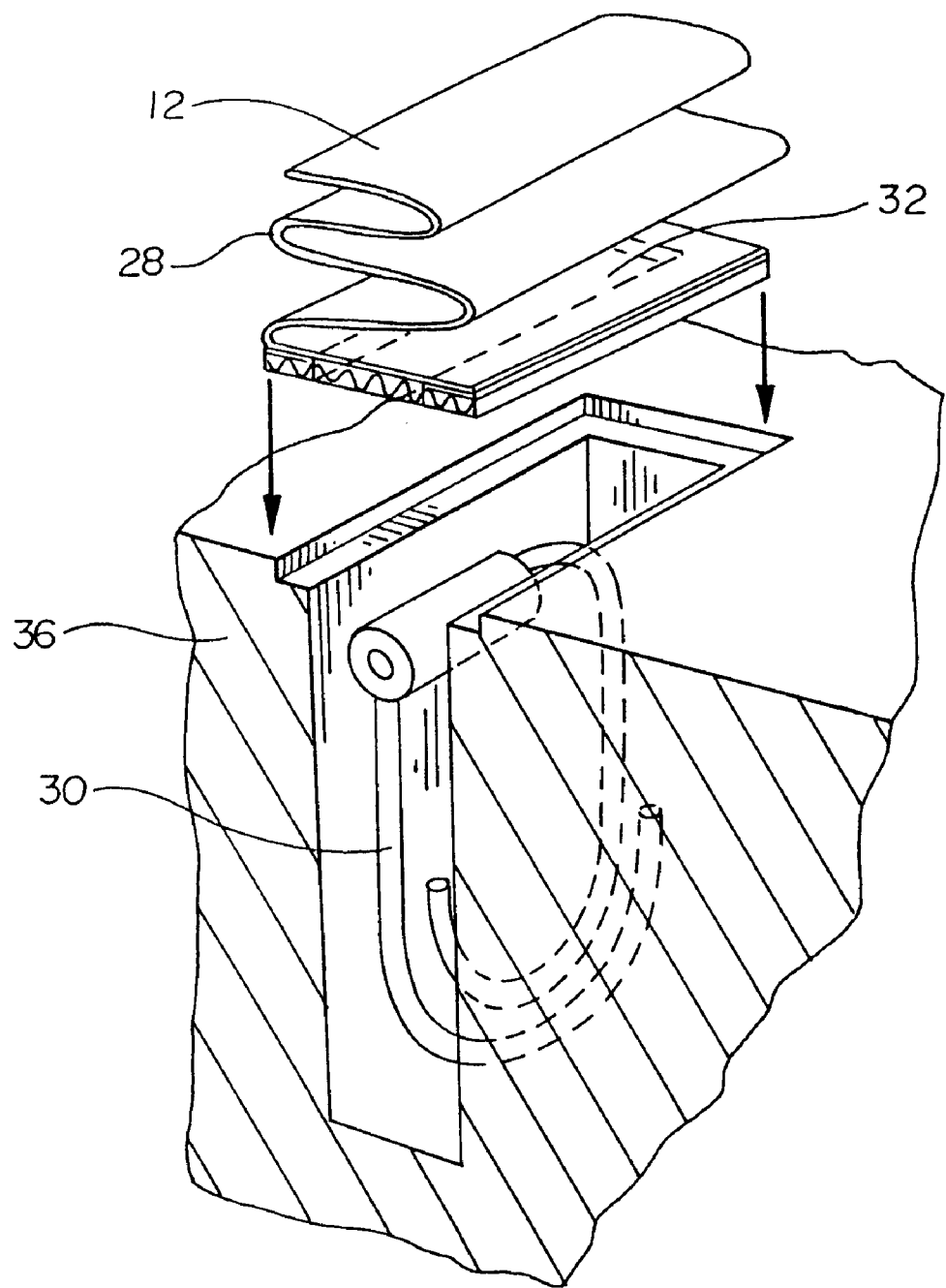
FIG. 3 is a perspective view of the device of the present invention and a partial cross sectional view of a sterilizer for use with the present invention with a perspective view of a sterilizable item inside the sterilizer.

Referring to FIGS. 1 through 3, the device 10 in accordance with the present invention broadly includes a pouch 12 and a support element 14. The device may also include a cover 16. Tape 18 may be used to attach the pouch 12 to the support element 14. Preferably, the tape 18 is two-sided adhesive tape. However, adhesive or any other method of fluid and bacterial tight attachment may be used. The cover 16 may include an adhesive strip 20 and a removable backing strip 22. However, a cover 16 is not necessary as long as a fluid tight attachment is maintained between the support element 14 and the sterilizer 36.

The pouch 12 is preferably a plastic flexible pouch having a front side 24 and a back side 26. The pouch 12 is preferably polyethylene film or a similar flexible, sealable film. The pouch 12 may be inflatable. The pouch 12 is preferably flexible or inflatable to save on storage space, allow easier attachment to the sterilizer 36, and to allow ease in retrieving the sterilizable item 30 from the sterilizer 36. A pouch 12 that is flexible can be folded, sterilized, and stored using much less space than if the pouch 12 were of rigid construction. The device 10 may be folded into a flat compact package. A pouch 12 that is flexible may also be attached to the sterilizer 36 without taking up additional sterilizer space. A pouch 12 that is flexible allows the user to reach into the sterilizer 36 through the frangible opening 32 to retrieve the sterilizable item 30. However, the pouch 12 could be of rigid construction, if the sterilizable item 30 was automatically retrieved after sterilization from the sterilizer 36 to the pouch 12. Such automation would eliminate the need to manually retrieve the sterilizable item 30.

The sides 24, 26 of the pouch 12 are preferably sealed along the perimeter 50 thereof. The sides 24, 26 are preferably polyethylene film sealed at the edges by heat bonding, adhesive, or other methods of fluid tight sealing. The sides 24, 26 are preferably rectangular, however, other shapes could be used. The pouch 12 defines a compartment 28 therewithin to hold a sterilizable item 30.

The pouch 12 includes a frangible opening 32, preferably a rectangularly shaped scored portion 34 cut into the front side 24 of the pouch 12. The scored portion 34 could be any shape that would allow passage of the sterilizable item 30 into the pouch and could be located on other parts of the pouch 12. Temporary seals other than scoring such as resealable openings or adhesives may be used for the frangible opening 32 as well. The frangible opening 32 could be any opening that would allow the compartment 28 to remain sterile and allow passage of the sterilizable item 30 from the sterilizer 36 into the compartment 28 after sterilization.

The support element 14 is for fluid attachment of the pouch 12 to a sterilizer 36. The support element 14 fluidly attaches the pouch 12 to the sterilizer 36. The support element 14 is preferably rigid. However, the support element 14 may be flexible as long as it provides fluid attachment between the pouch 12 and the sterilizer 36. The support element 14 may simply be adhesive between the pouch 12 and the sterilizer 36.

The support element 14 is preferably attached to the pouch 12 along a perimeter 52 of the frangible opening 32. However, the attachment may be anywhere circumscribing and fluidly attaching the support element 14 to the pouch 12. The support element 14 may be formed integrally with the pouch 12, particularly if the pouch 12 is of rigid construction. For example, the frangible opening 32 may be formed as part of the structure of the support element 14 instead of the sides 24, 26. The frangible opening 32 would still be part of the pouch 12 defining a compartment 28 and the remainder of the structure of the support element 14 would be integrally attached to the pouch 12.

The support element 14 defines a window 38 thereupon. Preferably, the window 38 is a perforated opening with a knockout piece 44. The window 38 provides an opening for the user to reach through to retrieve the sterilizable item 30 after it has been sterilized. The support element 14 may include a knockout piece 44 that is temporarily attached by perforations inside the window 38. Either one or both the pouch 12 and the support element 14 may include temporarily closed openings. The pouch 12 may have a frangible opening 32 and the support element 14 may have a knockout piece 44. However, the window 38 may be an opening without a knockout piece 44.

The support element 14 is preferably rectangularly shaped. However, the support element 14 may be any shape that fluidly connects the pouch 12 to the sterilizer 36. For example, the support element 14 could be square, circular, or irregularly shaped. Preferably, the support element 14 is comprised of rigid cardboard. However, the support element 14 could be constructed of plastic, paper, adhesive, or any combination of these. Preferably, the support element 14 is adhesively attached along the perimeter 54 thereof to the front side 24 of the pouch 12 along a perimeter 52 of the frangible opening 32. However, the support element 14 may be attached to the pouch 12 along any path circumscribing the frangible opening 32. Tape 18 may be used to attach the pouch 12 to the support element 14. Preferably, the tape 18 is two-sided adhesive tape. However, adhesive, bonding, or any other method of fluid tight attachment may be used to attach the pouch 12 to the support element 14.

The device 10 may also include a cover 16. The cover 16 may include an adhesive strip 20 and a removable backing strip 22. The cover 16 may include a back portion 40 and a front portion 42. The back portion 40 may be in adhesive contact with substantially the area of the window 38 for ensuring that the knockout piece 44 remains attached to the support element 14 until broken by the user.

Preferably, the cover 16 is resistant to sterilants and disinfectants, particularly performic acid sterilants. The cover 16 is preferably an adhesive backed label. The adhesive side being the back portion 40 of the cover 16 and the label side being the front portion 42 of the cover 16. The cover 16 is preferably thin enough so that it may be easily broken so that the user may retrieve the sterilizable item 30 from the sterilizer 36.

The cover 16 may include an adhesive strip 20. The adhesive strip 20 is for fluid attachment of the device 10 to the sterilizer 36. The adhesive strip 20 may be integrally formed with the cover 16. For example, the cover 16 may have adhesive on both the back portion 40 and the front portion 42 with a removable backing strip 22 attached to the front portion 42. Or, the adhesive strip 20 may be formed separately and attached to the front portion 42 of the cover 16. The adhesive strip 20 may have a top side 46 and a bottom side 48. The bottom side 48 is adhesively attached to the cover 16, preferably along a perimeter 56 of the front portion 42 of the cover 16. However, the adhesive strip 20 may be attached to the cover 16 along any path circumscribing the window 38. Preferably, the adhesive strip 20 is two-sided adhesive tape. However, adhesive, bonding, or any other method of fluid tight attachment may be used.

The top side 46 of the adhesive strip 20 preferably has a removable backing strip 22. The removable backing strip 22 may be removed just prior to fluid attachment of the device 10 to a sterilizer 36. The removable strip 22 protects the adhesive strip 22 prior to use.

In Operation

In operation, the device and method of the present invention may be used to provide a sterile packaging system. Referring to FIGS. 1 to 9, the method in accordance with the present invention broadly includes: a) providing a pouch 12 defining a sterile compartment 28, the pouch 12 having a frangible opening 32; b) providing a sterilizer 36; c) providing a sterilizable item 30; d) causing a fluid tight connection between the sterilizer 36 and the pouch 12, the fluid tight connection having exposed surfaces 58; e) sterilizing the exposed surfaces 58 within the fluid tight connection with the sterilizer 36; f) sterilizing the sterilizable item 30 with the sterilizer 36; g) breaking open the frangible opening 32; h) passing the sterilizable item 30 through the frangible opening 32 into the sterile compartment 28; and i) sealing the sterilizable item 30 inside the sterile compartment 28.

The device 10 is placed in a TYVEK® overwrap and sterilized with ETO, gamma irradiation or other means and sold to the end user.

The device 10 is removed from the sterile TYVEK® overwrap and the removable backing strip 22 is removed from the top side 46 of the adhesive strip 20. The cover 16, which is adhesively in contact with the window 38 and knock out piece 44, is placed over a basin of a sterilizer 36 (such as an endoscope reprocessing machine) containing a sterilizable item 30 (such as an endoscope) that has not yet been sterilized. The device 10 is clamped down to ensure that the adhesive strip 20 provides a fluid tight seal around the device 10/sterilizer 36 interface. During sterilization of the sterilizable item 30, the cover 16 comes into contact with sterilant thus ensuring that the exposed surfaces 58 of the cover 16 are sterile. The operator manually punches the knock out piece 44 out of the window 38 into the basin of the sterilizer 36. An air dry cycle of the sterilizer 36 then inflates the pouch 12. The sterilizer 36 may also use an inflation cycle without drying. The operator reaches down into the basin of the sterilizer 36 pushing the pouch 12 inside out, grasps the endoscope or sterilizable item 30 and pulls the sterilizable item 30 into the pouch 12, returning the pouch 12 to its original position. The pouch 12 is sealed by a sealer 60 such as a bar sealer at a point between the window 38 and the sterilizable item 30 contained in the sterile compartment 28. The pouch 12 is then cut proximal to the seal 62 and the sterilizable item 30 may be stored in a sterile condition until use.

The device 10 is preferably packaged with an overwrap and sterilized using ethylene oxide or gamma irradiation sterilization. The inside of the compartment 28 defined by the pouch 12, and interior portions of the device 10 such as beneath the cover 16 and the frangible opening 32 are sterile.

As shown in FIG. 3, the device 10 may be fluidly attached to a sterilizer 36 causing a fluid and microbial tight connection between the sterilizer 36 and the pouch 12. The support element 14 provides a fluid tight seal with the sterilizer 36. The support element 14 may be held in place with a clamp as shown in FIG. 4. Once the device 10 is fluidly attached to the sterilizer 30, the sterilizable item 36 and the exposed surfaces 58 of the device 10 within the fluid tight connection are sterilized. Therefore, all interior portions of the device 10 remain sterilized and any exterior surfaces of the device 10 either remain outside the sterile area of the sterile packaging system or are exposed surfaces 58 within the fluid tight connection that are sterilized by the sterilizer 36.

The sterilizable item 30 is sterilized by the sterilizer 36. The sterilizable item 30 may be any device, for example medical or dental devices. The sterilizer 36 may be any type of sterilizer including liquid chemical, gas, or steam. Preferably, the sterilizer 36 is a liquid chemical sterilizer for endoscopes.

As shown in FIGS. 5 through 7, the frangible opening 32 is broken open so that the sterilizable item 30 may be passed through the frangible opening 32 into the sterile compartment 28. The frangible opening 32 may be broken open before the sterilizable item 30 is sterilized. However, this creates a larger area to sterilize and may waste sterilant. In addition, the sterilizable item 30 may be retrieved into the pouch 12 before sterilization as well; however, this again creates a larger volume to sterilize, which may waste sterilant.

Breaking open the frangible opening 32 and passing the sterilizable item 30 through the frangible opening 32 into the sterile compartment 28 is preferably accomplished by the user by forcing their hand through the frangible opening 32 to break it open and reaching down into the sterilizer 36 and grasping the sterilizable item 30. The pouch 12 continually provides a sterile barrier between the users hand and the sterilizable item 30 while the pouch 12 is turned inside out so that the user's hand may reach into the sterilizer 36 and grasp the sterilizable item 30. The sterilizable item 30 is retrieved out of the sterilizer 36 and into the pouch 12. The pouch 12 is returned to its original position as the sterilizable item 30 is retrieved.

Figure 8:
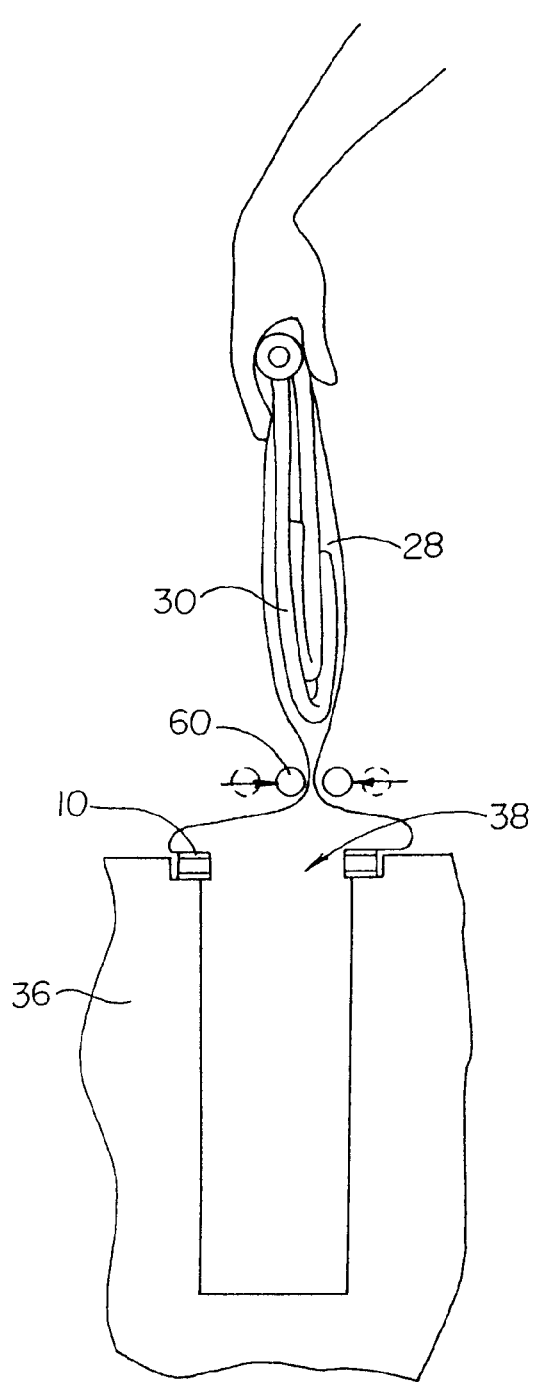
FIG. 8 is a is a partial cross sectional perspective view of a sterilizer with the device of the present invention attached to the sterilizer with a sterilizable item retrieved into the sterile compartment and a bar sealer in an open position ready for attachment to the device of the present invention.
Figure 9:
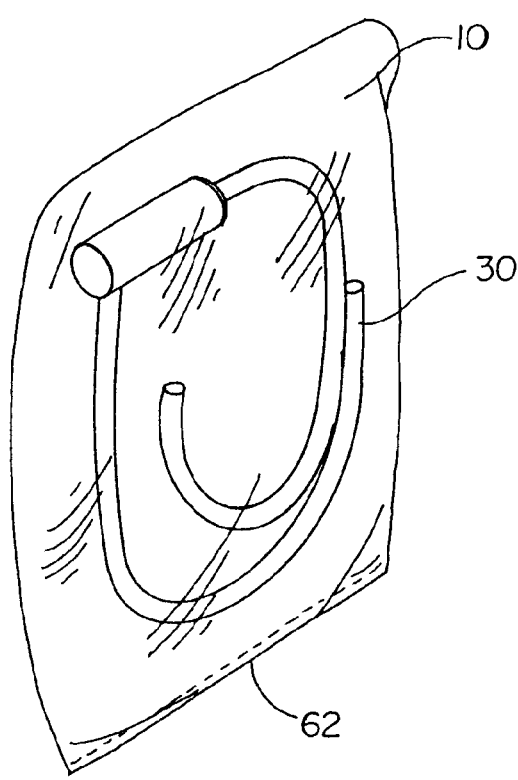
FIG. 9 is a partial cross sectional view of a sterilizer and the device of the present invention with a sealed pouch ready for removal from the sterilizer.

Once the sterilizable item 30 has been sterilized and retrieved into the sterile compartment 28, the pouch 12 is sealed. Preferably, the pouch 12 is sealed using a sealer 60, such as a bar sealer, as shown in FIGS. 8 and 9. However, other methods of resealing the pouch 12 may be used such as resealable closures, fluid tight ties, adhesives, or bonding. These closures could be easily manipulated within the sterile compartment 28 to create a sterile seal 62.

Once the device 10 is sealed it may be removed from the sterilizer 36 to be stored ready for use. The device 10 may be removed by cutting the pouch 12 proximate to the seal 62. In addition, the support element 14 may remain with the device 10 for storage. The device 10 and method of the present invention maintains the sterilizable item 36 in a portable sterile package ready for storage or use.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

I claim:

1. A packaging system for a sterilizable item comprising:
    a) a pouch having a frangible opening, said pouch defining a sterile compartment therein to hold a sterilizable item;
    b) a support element for fluid attachment to a sterilizer, said support element defining a window thereupon, said support element attached to said pouch along a perimeter of said frangible opening; and
    c) a cover, said cover having a front portion and a back portion, said back portion adhesively in contact with said window.

2. The packaging system of claim 1 wherein said pouch is flexible.

3. The packaging system of claim 1 wherein said pouch is inflatable.

4. The packaging system of claim 1 wherein said pouch has a front side and a back side sealed along a perimeter thereof.

5. The packaging system of claim 4 wherein said frangible opening is a scored portion cut into one of said sides of said pouch.

6. The packaging system of claim 5 wherein said scored portion is rectangular and cut into said front side of said pouch.

7. The packaging system of claim 4 wherein said pouch has a front side and a back side sealed along a perimeter thereof, wherein said support element is adhesively attached along a perimeter thereof to said front side of said pouch along a perimeter of said frangible opening.

8. The packaging system of claim 1 wherein said support element is rigid.

9. The packaging system of claim 1 wherein said support element is rigid cardboard and is rectangularly shaped.

10. The packaging system of claim 1 wherein said window is a perforated window with a knock out piece positioned in said window.

11. The packaging system of claim 1 further comprising an adhesive strip, said adhesive strip having a top side and a bottom side, said bottom side adhesively attached along a perimeter of said window.

12. The packaging system of claim 11 further comprising a removable backing strip attached to said top side of said adhesive strip.

13. The packaging system of claim 1 wherein said window is a perforated window with a knock out piece positioned in said window, and wherein said cover is in contact with substantially the area of said window for ensuring that said knockout piece remains attached to said support element until broken open.

14. The packaging system of claim 1 further comprising an adhesive strip, said adhesive strip having a top side and a bottom side, said bottom side of said adhesive strip attached along a perimeter of said front portion of said cover.

15. The packaging system of claim 14 further comprising a removable backing strip attached to said front side of said adhesive strip.

16. A packaging system for a sterilizable item comprising:
    a) an inflatable pouch having a front side and a back side sealed along a perimeter thereof, said pouch defining a compartment therein to hold a sterilizable item;
    b) said front side of said pouch including a scored portion cut into said front side of said pouch;
    c) a rigid cardboard support element defining a perforated window with a knockout piece, said support element adhesively attached along a perimeter thereof to said front side of said pouch along a perimeter of the scored portion;
    d) a cover including a front portion and a back portion, said back portion adhesively in contact with substantially the area of said window for ensuring that said knockout piece remains attached to said support element until broken; and
    e) an adhesive strip including a top side and a bottom side, said bottom side of said adhesive strip adhesively attached along a perimeter of said front portion of the cover, said top side including a removable backing strip.

\* \* \* \* \*

UNITED STATES PATENT AND TRADEMARK OFFICE
CERTIFICATE OF CORRECTION

PATENT NO.     : 6,234,310 B1
DATED          : May 22, 2001
INVENTOR(S)    : Richard P. Goldhaber It is certified that error appears in the above-identified patent and that said Letters Patent is hereby corrected as shown below:

<u>Title page,</u>
Insert Item -- [73] Assignee: Minntech Corporation, Minneapolis, MN --

Signed and Sealed this

Thirtieth Day of September, 2003

JAMES E. ROGAN
*Director of the United States Patent and Trademark Office*